(12) United States Patent
Bhattacharyya et al.

(10) Patent No.: US 8,552,217 B2
(45) Date of Patent: Oct. 8, 2013

(54) ISOCYANATE MANUFACTURE

(75) Inventors: Subha Bhattacharyya, Metuchen, NJ (US); Scott Guelcher, Franklin, TN (US); Damodaragounder Gopal, Highland Heights, OH (US); Marco Burello, Cleveland, OH (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 250 days.

(21) Appl. No.: 13/021,626

(22) Filed: Feb. 4, 2011

(65) Prior Publication Data

US 2012/0202961 A1    Aug. 9, 2012

(51) Int. Cl.
*C07C 263/10*    (2006.01)
(52) U.S. Cl.
USPC .................. 560/347; 560/336; 560/338
(58) Field of Classification Search
USPC ................... 528/85; 560/347, 336, 338
See application file for complete search history.

(56) References Cited

U.S. PATENT DOCUMENTS 6,399,822 B1 *   6/2002   Eckert et al. ............ 562/847
2011/0275854 A1 * 11/2011  Daussin et al. ........... 560/347

OTHER PUBLICATIONS

Eckert et al; Organic process research and development, 2010, 14, 1501-1505.*
Eckert et al; Angewandte Chemie (international ed.), 26 (9), 1987.*

* cited by examiner

*Primary Examiner* — Johann R. Richter
*Assistant Examiner* — Pancham Bakshi
(74) *Attorney, Agent, or Firm* — Sorell Lenna & Schmidt LLP

(57) ABSTRACT

The present invention encompasses the finding that improvements can be achieved in manufacture of isocyanates through the use of a substitute for or a precursor of phosgene. Methods and compositions utilized in accordance with the present invention can be useful in situations in which it is difficult to use phosgene, and in particular gaseous phosgene. In some embodiments, a substitute for or a precursor of phosgene used in accordance with the present invention for preparing isocyanates is or comprises diphosgene ($ClCO_2CCl_3$).

20 Claims, 1 Drawing Sheet

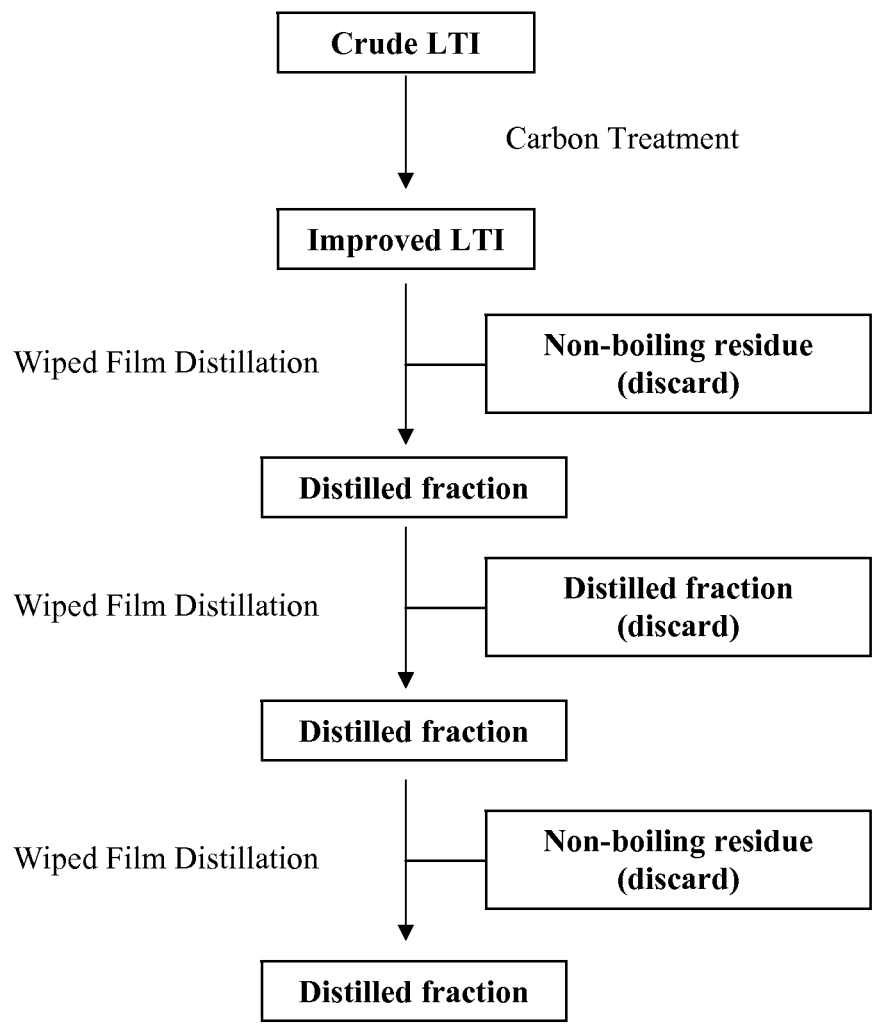

ISOCYANATE MANUFACTURE

BACKGROUND

Isocyanates are compounds that contain an —N=C=O moiety and are typically highly reactive. Reactions between isocyanate compounds and alcohol compounds (i.e., compounds with an —OH moiety) generate polyurethanes, which in turn are used in a wide range of consumer products including, for example, foams, adhesives, insulation materials, surface coatings, etc.

Isocyanates are typically manufactured by reacting an amine compound (i.e., a compound with an —NH$_2$ moiety) with phosgene (COCl$_2$). Phosgene, however, is highly toxic and difficult to handle. Phosgene was even used as a chemical weapon during World War I. Facilities capable of handling, or willing to handle, phosgene are limited.

SUMMARY

The present invention encompasses the finding that improvements can be achieved in manufacture of isocyanates through the use of a substitute for or a precursor of phosgene. In some embodiments, the invention provides methodologies for preparing isocyanates by using diphosgene (ClCO$_2$CCl$_3$). Moreover, the present invention provides methodologies for preparing isocyanates at elevated temperatures (e.g., within the range of 125-310° C.). In some embodiments, the present invention provides methodologies for preparing lysine ester triisocyanate (LTI) by reacting an amine and/or its salt form with disphosgene at elevated temperatures. In particular, the present invention provides methodologies for preparing LTI by reacting lysin-β-aminoethyl ester trihydrochloride (i.e., trihydrochloride salt) with disphosgene at elevated temperatures.

Methods and compositions utilized in accordance with the present invention can be useful in situations in which it is difficult to use phosgene, and in particular gaseous phosgene. In some embodiments, a substitute for or a precursor of phosgene used in accordance with the present invention for preparing isocyanates is or comprises diphosgene (ClCO$_2$CCl$_3$). For example, a two-reactor system can be used where disphogene is added in a controlled manner to a heated and stirred suspension in a reactor. In some embodiments, such a suspension comprises a catalyst (e.g., activated carbon, alumina, etc.). In some embodiments, a suspension comprises such a catalyst in a solvent, for example, o-dichlorobenzene. Without wishing to be bound to any particular theory, it is believed that such a catalyst breaks disphogene to produce phosgene gas, which can be transferred to another reactor containing a suspension of an amine at approximately 135° C. In some embodiments, such an amine is or comprises a salt form (e.g., trihydrochloride salt). In some embodiments, a suspension of an amine comprises a solvent, for example, 1,2-dichlorobenzene.

The present invention further encompasses recognition that, alternatively or additionally, disphogene surprisingly can be added in a controlled manner directly to a heated and stirred suspension of an amine in a reactor at approximately 135° C. In some embodiments, a reaction is performed at atmospheric pressure. In some embodiments, a reaction is performed at elevated pressure. In certain embodiments, a reaction is performed at elevated pressure and a solvent with a low boiling point is used for ease of product isolation. In some embodiments, an amine is or comprises a salt form (e.g., trihydrochloride salt). In some embodiments, a suspension of an amine comprises a solvent, for example, 1,2-dichlorobenzene. Without wishing to be bound to any particular theory, it is believed that the breaking of disphogene can occur in situ at approximately 135° C. and react with an amine to produce an isocyanate.

Among other things, the present invention encompasses development of methods to preparation of an isocyanate with high purity. In some embodiments, an intermediate containing low levels of impurity is used to make such an isocyanate. For example, LTI can be produced with low levels of 2,6-diisocyanoto-hexanoic acid methyl ester ("methyl ester") impurity by using lysin-β-aminoethyl ester trihydrochloride (i.e., trihydrochloride salt) that contains low levels of methyl ester impurity. In some embodiments, methyl ester impurity is removed by distillation. In some embodiment, methyl ester impurity is reduced to less than 1%.

It is also recognized in the present invention, among other things, that fractional removal of impurity improves crude materials. In some embodiments, fractional removal of methyl ester impurity allows for use of commercially available crude LTI containing high levels of impurity (e.g., greater than 3%). In certain embodiments, impurity is fractionally removed by distillation.

Other aspects, features and advantages will be apparent from the description of the embodiments thereof and from the claims.

DEFINITIONS

The term "polyurethane" and "PUR" as used herein, is intended to include all polymers incorporating more than one urethane group (—NH—CO—O—) in the polymer backbone. Polyurethane materials, in some embodiments, refer to the compositions formed by the reaction of a polyisocyanate (such as a diisocyanate) and a polyol (such as a diol), optionally with any additional components. For example,

HO—R$_1$—OH  +  OCN—R$_2$•NCO  ⟶

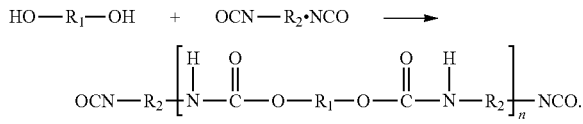

In some embodiments, polyurethane materials refer to the compositions comprising a polyisocyanate (such as a diisocyanate) and a polyol (such as a diol), and optionally a catalyst.

The term "phosgene substitute" as used herein, refers to a compound able to replace phosgene as a reagent in syntheses, or able to specifically bring about the basic phosgene functions as a carbonylating agent. In some embodiments, a phosgene substitute is or comprises a phosgene equivalent. The general structure, $Z^1$—CO—$Z^2$ illustrates the main structural characteristic of phosgene equivalents, i.e., the presence of the carbonyl (or carbonyl precursor) group flanked by two leaving groups ($Z^1$ and $Z^2$). In some embodiments, $Z^1$ and/or $Z^2$ is halo, alkoxy, aryloxy, imidazolyl, triazolyl, etc. $Z^1$ and $Z^2$ can be identical or different, thus generating symmetrical or unsymmetrical phosgene equivalents, respectively. Exemplary phosgene substitutes may includes but are not limited to diphosgene, triphosgene, 1,1-carbonyldiimidazole, thionyl chloride, bis(nitrophenyl)carbonate, di-tert-buyl dicarbonate, etc. More exemplary phosgene equivalents and/or substitutes can be found on pages 37-40, in "Phosgenations—a handbook" by L. Cotarca, et al (2004), which is incorporated herein by reference. In some embodiments, a phosgene substitute is or comprises a phosgene precursor. A phosgene precursor, in general, refers to a compound able to convert or generate phosgene.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N(R$^†$)— as in N-substituted pyrrolidinyl.

The term "unsaturated", as used herein, means that a moiety has one or more units of unsaturation.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring".

As described herein, compounds used in accordance with the present invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^●$, -(haloR$^●$), —(CH$_2$)$_{0-2}$OH, —(CH$_2$)$_{0-2}$OR$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●$$_2$, —NO$_2$, —SiR$^●$$_3$, —OSiR$^●$$_3$, —C(O)SR$^●$, —(C$_{1-4}$ straight or branched alkylene)C(O)OR$^●$, or —SSR$^●$ wherein each R$^●$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^●$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. A suitable tetravalent substituent that is bound to vicinal substitutable methylene carbons of an "optionally substituted" group is the dicobalt hexacarbonyl cluster represented by

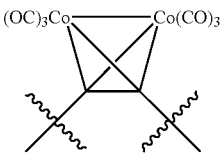

when depicted with the methylenes which bear it.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

DESCRIPTION OF DRAWING

FIG. 1 illustrates removal of 1,2-dichlorbenzene and "methyl ester" by Wiped film distillation.

DETAILED DESCRIPTION OF CERTAIN EMBODIMENTS

As used herein and in the appended claims, the singular forms "a," "an" and "the" include plural references unless the content clearly dictates otherwise. All publications, patent applications, patents, and other references mentioned herein are incorporated by reference in their entirety.

Synthesis of Isocyanates

Isocyanate is the functional group of —N=C=O. Any compound, as understood by one of ordinary skill in the art, which contains an isocyanate group/moiety may be referred to in brief as an isocyanate. An isocyanate may have one or more isocyanate groups/moieties.

Typically, isocyanates are generated from amines reacting with phosgene. The synthesis of isocyanates illustrates the electrophilic character of phosgene and its use in introducing the equivalent of "CO$^{2+}$":

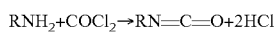

RNH$_2$+COCl$_2$→RN=C=O+2HCl where R can be an alkyl, an aryl, etc. Such reaction can be conducted in the presence of a base such as pyridine that absorbs the by product, hydrogen chloride.

Among other things, the present invention provides methods for the synthesis of isocyanates. Methodologies, tools and/or reagents for disclosed herein can be used in manufacturing any isocyanate. In some embodiments, an isocyanate is produced by a reaction between an amine reagent and a phosgene substitute and/or precursor.

Amines

Amines used in accordance with the present invention may include an aliphatic amine, an aromatic amine, a salt form thereof, or any combinations thereof. Such an amine can comprise one or more amino functional groups. In some embodiments, an amine is or comprises a primary amine to generate an isocyanate. In some embodiments, an amine has two or three primary amino groups.

In some embodiments, methodologies, tools and/or reagents utilized in accordance with the present invention are used in synthesis of isocyanates include multi-isocyanate compounds. Exemplary multi-isocyanate compounds include, but are not limited to, lysine diisocyanate, an alkyl ester of lysine diisocyanate (for example, a methyl ester or an ethyl ester), lysine triisocyanate, hexamethylene diisocyanate, isophorone diisocyanate 4,4'-dicyclohexylmethane diisocyanate (H$_{12}$MDI), cyclohexyl diisocyanate, 2,2,4-(2,2,4)-trimethylhexamethylene diisocyanate (TMDI), dimers prepared form aliphatic polyisocyanates, trimers prepared from aliphatic polyisocyanates and/or mixtures thereof.

In some embodiments, methodologies, tools and/or reagents utilized in accordance with the present invention are used in synthesis of lysine ester triisocyanate (LTI). In some embodiments, synthesis of LTI in accordance with the present invention comprises reacting a phosgene substitute or precursor with an amine of the formula I:

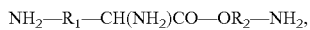

NH$_2$—R$_1$—CH(NH$_2$)CO—OR$_2$—NH$_2$, wherein R$_1$ and R$_2$, respectively and independently, represent an aliphatic or an aryl group.

In some embodiments, an amine reagent is provided in salt form. Examples of the salt of an amine include, but are not limited to inorganic acid salts, such as hydrochlorides, sulfates, nitrates, and the like, and organic acid salts, such as p-toluenesulfonates and the like. In certain embodiments, hydrochlorides of an amine is utilized in accordance with the present invention. In certain embodiments, lysin-β-aminoethyl ester trihydrochloride (i.e., trihydrochloride salt) is utilized in accordance with the present invention to produce LTI. A reaction between the triamine or the salf with phosgene is disclosed in Yamasaki, et al. U.S. pat. Application US2006/0167303, which is incorporated herein by reference.

As defined generally above, the R$_1$ and/or R$_2$ moieties of formula I can be any aliphatic or aryl group.

In some embodiments, the R$_1$ moiety of formula I is an aliphatic group. In some embodiments, the R$_2$ moiety of formula I is an aliphatic group. In some embodiments, the $R_1$ moiety of formula I is an aryl group. In some embodiments, the $R_2$ moiety of formula I is an aryl group.

In some embodiments, the $R_1$ and $R_2$ moieties of formula I are both aliphatic groups. In some embodiments, the $R_1$ and $R_2$ moieties of formula I are both aryl groups. In certain embodiments, the $R_1$ and $R_2$ moieties of formula I are different groups, respectively. In still other embodiments, the $R_1$ and $R_2$ moieties of formula I are the same groups.

In some embodiments, the $R_1$ moiety of formula I is —$(CH_2)_4$—.

In some embodiments, the $R_2$ moiety of formula I is —$(CH_2)_2$—.

In some embodiments, the $R_1$ moiety of formula I is —$(CH_2)_4$— and the $R_2$ moiety of formula I is —$(CH_2)_2$—.

In certain embodiments, the $R_1/R_2$ moiety of the formula I is an optionally substituted aliphatic group, as described above. Examples include t-butyl, 5-norbornene-2-yl, octane-5-yl, acetylenyl, trimethylsilylacetylenyl, triisopropylsilylacetylenyl, and t-butyldimethylsilylacetylenyl. In some embodiments, said $R_1/R_2$ moiety is an optionally substituted alkyl group. In other embodiments, said $R_1/R_2$ moiety is an optionally substituted alkynyl or alkenyl group. When said $R_1/R_2$ moiety is a substituted aliphatic group, suitable substituents on $R_1/R_2$ include CN, $N_3$, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methyl-propargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, and 2-propargyldisulfanyl. In certain embodiments, the $R^1$ group is 2-(N-methyl-N-(ethynylcarbonyl)amino)ethoxy, 4-ethynylbenzyloxy, or 2-(4-ethynylphenoxy)ethoxy.

In certain embodiments, the $R_1/R_2$ moiety of formula I is an optionally substituted aryl group, as described above. Examples include optionally substituted phenyl and optionally substituted pyridyl. When said $R_1/R_2$ moiety is a substituted aryl group, suitable substituents on $R_1/R_2$ include CN, $N_3$, $NO_2$, —$CH_3$, —$CH_2N_3$, —$CH=CH_2$, —$C\equiv CH$, Br, I, F, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

Phosgene Substitutes and/or Precursors

Phosgene substitutes and/or precursors used in accordance with the present invention may include any phosgene equivalents such as a disphosgene, a triphosgene, etc, and any combination thereof. Phosgene utilized in accordance with the present invention may be provided via thermal dissociation of carbamic acid derivatives using chloroformates, disphenylcarbonate, or N,N'-carbonyldiimidazole, etc.

As defined above, a phosgene substitute and/or precursor can be a compound able to replace phosgene as a reagent in syntheses, or able to specifically bring about the basic phosgene functions as a carbonylating, agent.

Diphosgene is a chemical compound with the formula, $ClCO_2CCl_3$. Diphosgene is a colorless liquid at room temperature, and can be used as a phosgene source in many applications. Diphosgene can decompose very rapidly and quantitatively upon heating and/or upon catalysis, and in situ generated phosgene can react with a nucleophile. In accordance with the present invention, a nucleophile can be an amine including its salt form, which reacts with phosgene to produce an isocyanate.

As understood by these of ordinary skill in the art, under certain conditions, diphosgene can serve as a source of two equivalents of phosgene:

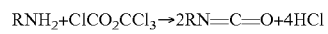

$$RNH_2 + ClCO_2CCl_3 \rightarrow 2RN=C=O + 4HCl$$

In some embodiments, triphosgene is used as a phosgene equivalent or a source of phosgene (i.e., a phosgene substitute). However, the present invention further encompasses the recognition that, in at least some embodiments, the use of triphosgene is not a desirable substitute for phosgene in LTI preparation.

In some embodiments, a phosgene substitute and/or precursor is provided in a liquid or a gas phase.

Reaction Conditions

In general, a phosgene substitute and/or precursor is used in place of phosgene to react with an amine in accordance with the present invention.

In some embodiments, a two-reactor system can be used where a phosgene substitute and/or precursor is added in a controlled manner in a first reactor. Such a reaction can contain a stirred suspension, at room temperature or at an elevated temperature. In some embodiments, a heated suspension comprises a catalyst, including but not limiting to activated carbon, alumina, a nitrogen compound (e.g., pyridine, quinoline, tetramethyl urea, or tertiary amines). In some embodiments, a heated suspension comprises such a catalyst in an inert solvent, such as an aromatic hydrocarbon (e.g., benzene, toluene, o-xylene, m-xylene, p-xylene and the like), a chlorinated aromatic hydrocarbon (e.g., chlorobenzene, o-dichlorobenzene, m-dichlorobenzene, p-dichlorobenzene and the like), a chlorinated aliphatic hydrocarbon (e.g., trichloroethane and the like), or a chlorinated alicyclic hydrocarbon (e.g., chlorocyclohexane). Without wishing to be bound to any particular theory, it is believed that a catalyst facilitates the conversion of a phosgene substitute and/or precursor to produce phosgene gas, which can be transferred to a second reactor containing a suspension of an amine.

Reaction of a phosgene substitute and/or precursor in a reactor can be carried out at an elevated temperature. A suspension in a first or a second reactor can be heated up to 260-310° C. In some embodiments, a phosgene substitute and/or precursor is added in a suspension in a first reactor at a temperature around 320° C., 310° C., 300° C., 290° C., 280° C., 270° C., 260° C., 250° C., 150° C., 140° C., 135° C., 130° C., 125° C., 120° C., 110° C., or in a range of any two values above. In certain embodiments, a phosgene substitute and/or precursor is added in a suspension in the presence of a catalyst in a first reactor at a temperature around 150° C., 140° C., 135° C., 130° C., 125° C., 120° C., 110° C., or in a range of any two values above. In some embodiments, such an elevated temperature is maintained for a phosgene substitute and/or precursor before and/or during the reaction with amine.

A phosgene gas produced in a first reaction can be transferred to a second reactor. In some embodiments, a phosgene gas produced in a first reaction is transferred to a second reactor via any additional reactors/components or steps, for purification or any other processing. In some embodiments, such a second reactor contains an amine to react with a phosgene gas produced in a first reaction. Such an amine can be in suspension.

In some embodiments, an amine is suspended or dissolved in an inert solvent, such as an aromatic hydrocarbon (e.g., benzene, toluene, o-xylene, m-xylene, p-xylene and the like), a chlorinated aromatic hydrocarbon (e.g., chlorobenzene, o-dichlorobenzene, m-dichlorobenzene, p-dichlorobenzene and the like), a chlorinated aliphatic hydrocarbon (e.g., trichloroethane and the like), or a chlorinated alicyclic hydrocarbon (e.g., chlorocyclohexane).

An amine in a second reactor can be heated at any suitable temperature or in a suitable range of temperature. In some embodiments, an amine in a second reactor can be heated at a temperature around 320° C., 310° C., 300° C., 290° C., 280° C., 270° C., 260° C., 250° C., 150° C., 140° C., 135° C., 130° C., 125° C., 120° C., 110° C., or in a range of any two values above. In certain embodiments, an amine in a second reactor can be heated at a temperature around 150° C., 140° C., 135° C., 130° C., 125° C., 120° C., 110° C., or in a range of any two values above.

As will be appreciated by these of ordinary skill in the art, reaction pressure of a first or a second reactor can be held at atmospheric pressure or at any suitable pressures. In some embodiments, reaction pressure of a first or a second reactor is held at an elevated pressure (e.g., greater than 1 atm, 1.2 atm. 1.5 atm, 2 atm, 3 atm, 5 atm, etc.). In some embodiments, reaction pressure of a first or a second reactor is held at an elevated pressure when a solvent with a low boiling point is used. Without wishing to be bound to any particular theory, the low boiling point of the solvent may allow its easy separation/isolation from products.

Alternatively or additionally, a phosgene substitute and/or precursor can be added directly in a controlled manner to a heated and stirred suspension of an amine in one-reactor system. In some embodiments, a suspension of an amine comprises such a catalyst in an inert solvent, such as an aromatic hydrocarbon (e.g., benzene, toluene, o-xylene, m-xylene, p-xylene and the like), a chlorinated aromatic hydrocarbon (e.g., chlorobenzene, o-dichlorobenzene, m-dichlorobenzene, p-dichlorobenzene and the like), a chlorinated aliphatic hydrocarbon (e.g., trichloroethane and the like), or a chlorinated alicyclic hydrocarbon (e.g., chlorocyclohexane). In some embodiments, a heated suspension comprises a catalyst, including but not limiting to activated carbon, alumina, a nitrogen compound (e.g., pyridine, quinoline, tetramethyl urea, or tertiary amines). Without wishing to be bound to any particular theory, it is believed that a catalyst facilitates the conversion of a phosgene substitute and/or precursor, and in situ generated phosgene can react with an amine to produce an isocyanate.

Reaction of such a one-reactor system can be carried out at an elevated temperature. A suspension in a reactor can be heated up to 260-310° C. In some embodiments, a phosgene substitute and/or precursor is added in a suspension of an amine at a temperature around 320° C., 310° C., 300° C., 290° C., 280° C., 270° C., 260° C., 250° C., 150° C., 140° C., 135° C., 130° C., 125° C., 120° C., 110° C., or in a range of any two values above. In certain embodiments, a phosgene substitute and/or precursor is added in a suspension in the presence of a catalyst in a first reactor at a temperature around 150° C., 140° C., 135° C., 130° C., 125° C., 120° C., 110° C., or in a range of any two values above. In some embodiments, such an elevated temperature is maintained for a phosgene substitute or precursor during the reaction with amine.

As will be appreciated by these of ordinary skill in the art, reaction of a one-reactor system can be performed at atmospheric pressure or at any suitable pressures. In some embodiments, reaction pressure of a reactor is held at an elevated pressure (e.g., greater than 1 atm, 1.2 atm. 1.5 atm, 2 atm, 3 atm, 5 atm, etc.). In some embodiments, reaction pressure of a reactor is held at an elevated pressure when a solvent with a low boiling point is used. Without wishing to be bound to any particular theory, the low boiling point of the solvent may allow its easy separation/isolation from products.

A phosgene substitute and/or precursor can be added until no more suspended amine (e.g., in a solid phase) is visible in a reaction containing such an amine. Subsequent concentration of resulting solution allows recovery of isocyanates.

In some embodiments, a phosgene substitute and/or precursor can be added in a controlled manner. For example, it is done by syringe-pump addition of a phosgene substitute and/or precursor to a suspension. Alternatively or additionally, a phosgene substitute and/or precursor can be added by dropping funnel. Without wishing to be bound to any particular theory, it is proposed that an addition by dropping funnel can eliminate the need for stringent control of addition rates.

Purification

Methodologies in accordance with the present invention can be used to prepare an isocyanate with high purity. In some embodiments, an isocyanate is purified before subsequent use.

In some embodiments, an intermediate containing low levels of impurity is used to make such an isocyanate. In some embodiments, an intermediate for making an isocyanate is or comprises lysin-β-aminoethyl ester trihydrochloride (i.e., trihydrochloride salt) that reacts with a phosgene substitute and/or precursor. For example, LTI can be produced with low levels of 2,6-diisocyanoto-hexanoic acid methyl ester ("methyl ester") impurity by using a trihydrochloride salt that contains low levels of methyl ester impurity. In some embodiments, methyl ester impurity is removed by distillation. In some embodiment, methyl ester impurity is reduced to less than 1%.

Additionally or alternatively, impurity in crude materials (i.e., an isocyanate) can be fractionally removed. In certain embodiments, impurity is fractionally removed by distillation. In some embodiments, impurity in a commercially available isocyanate (e.g., LTI) is purified according to the present invention. For example, fractional removal of methyl ester impurity allows for use of commercially available crude LTI containing high levels of impurity (e.g., greater than 3%). In some embodiments, produced isocyanate according to the present invention is purified by fractional removal of impurity. In certain embodiments, produced isocyanate according to the present invention is purified by fractional removal of methyl ester impurity.

Use of Isocyanates

Isocyanates generated by methods in accordance with the present invention, can be purified and used to form urethane linkage with a hydroxyl functional group. For example, if a component having two or more hydroxyl groups (i.e., polyols) is reacted with an isocyanate containing two or more isocyanate groups (i.e., polyisocyanante), polymer chains are formed, known as polyurethane (PUR).

Polyurethanes can be made by reacting together the components of a two-component composition, one of which includes a polyisocyanate and a polyol. It is to be understood that by "a two-component composition" it means a composition comprising two essential types of polymer components. In some embodiments, such a composition may additionally comprise one or more other optional components.

An exemplary reaction for polyurethane synthesis using LTI is illustrated below, where an isocyanate and a polyester polyol react to form urethane bonds. In some embodiments, $R_1$, $R_2$ and $R_3$, are respectively, oligomers of caprolactone, lactide and glycolide.

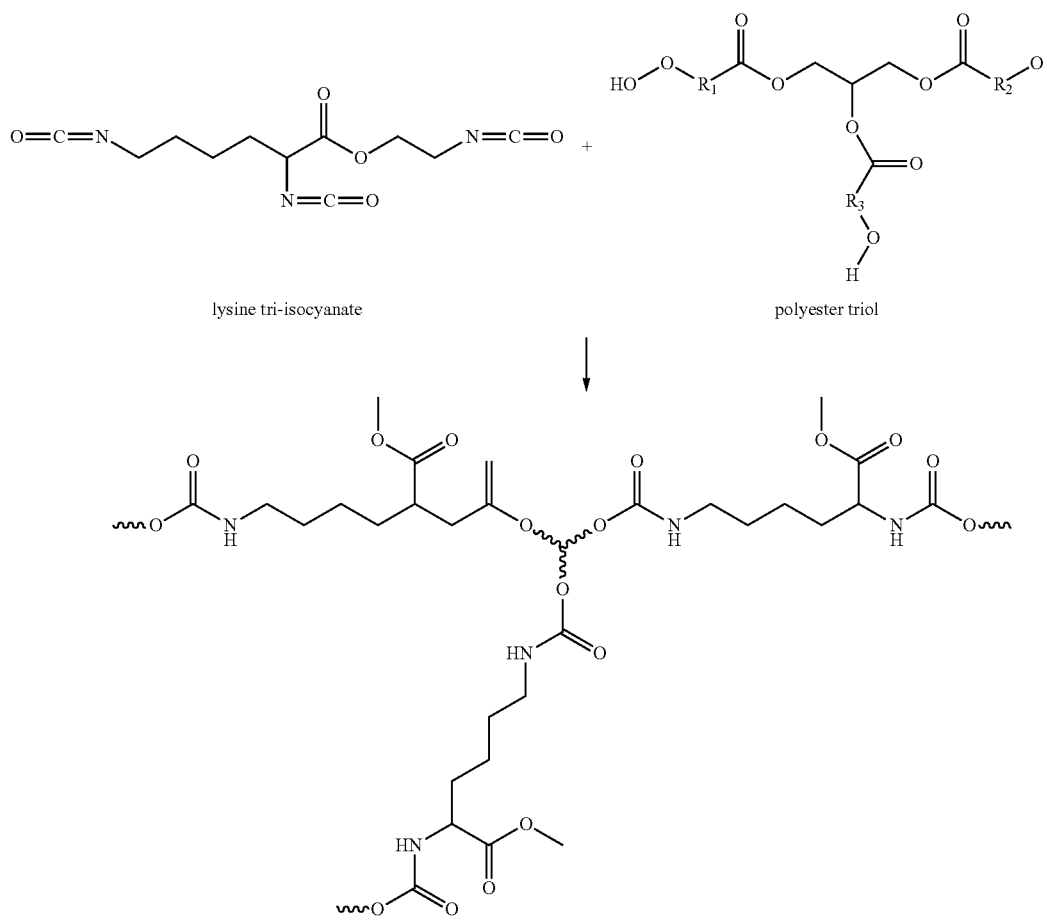

lysine tri-isocyanate polyester triol

Depending on reaction condition, a product of reacting an isocyanate with a polyol can be a polymer that are fully polymerized, or a pre-polymer that can be further polymerized. In some embodiments, a pre-polymer produced from an isocyanate is used in a two-component composition to make polyurethane materials. A pre-polymer is a low molecular weight oligomer typically produced through step growth polymerization. For example, a polyol and an excess of polyisocyanate may be polymerized to produce isocyanate terminated prepolymer that may be combined then with a polyol to form a polyurethane. In some embodiments, a polyol reacted with an excess of polyisocyanate to make a pre-polymer, includes, but are not limited to, glycerol, pentaerythritol, dipentaerythritol, tripentaerythritol, 1,2,4-butanetriol, trimethylolpropane, 1,2,3-trihydroxyhexane, myo-inositol, ascorbic acid, a saccharide, or sugar alcohols (e.g., mannitol, xylitol, sorbitol etc.).

In certain embodiments, such a polyol to make pre-polymer is a polymer containing more than one hydroxyl groups, such as polyethylene glycol (PEG). In some embodiments, polyols have a molecular weight of no more than 1000 g/mol. In some embodiments, polyols have a rang of molecular weight between about 100 g/mol to about 500 g/mol. In some embodiments, polyols have a range of molecular weight between about 200 g/mol to about 400 g/mol. In certain embodiments, polyols (e.g., PEG) have a molecular weight of about 200 g/mol. For example, a LTI-PEG pre-polymer using PEG-200 (i.e., having an average molecular weight of 200 g/mol) was synthesized and demonstrated in Example 5.

As will be appreciated by these of ordinary skill in the art, reacting an isocyanate with a polyol can result in a mixture of products. For example, polyurethane materials can be produced by reacting at least one isocyanantes with at least one polyol. A product can refer to a composition formed by the reaction of an isocyanate (e.g., LT1) and a polyol (e.g., PEG). In some embodiments, a product can include a series of polymer materials having a distribution of various molecule weight. In some embodiments, an average molecule weight is used as understood in the art.

Polyurethanes (PUR) are a useful class of biomaterials to be included in composite materials, for example, with bone particles as described in US Patent Application Publication No. 2010-0112032, the content of which is incorporated herein by reference. Such composite materials may be prepared by contacting an isocyanate-terminated prepolymer (e.g, a LTI-PEG pre-polymer) with a polyol (e.g., a polyester polyol), and optionally with addition of water, a catalyst, a stabilizer, a porogen, PEG, an agent to be delivered, etc.

These and other aspects of the present invention will be further appreciated upon consideration of the following Examples, which are intended to illustrate certain particular embodiments of the invention but are not intended to limit its scope, as defined by the claims.

EXAMPLES

Example 1

Synthesis of Lysine-β-aminoethyl Ester Trihydrochloride ("Trihydrochloride Salt")

Di-Boc lysine (ref. 22117-48)

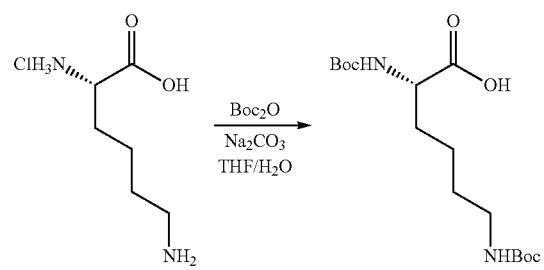

L-lysine (450 grams, 2.46 mol) was charged to a 12 liter flask followed by water (3.6 liters) and THF (3.6 liters). Sodium carbonate (540 grams, 5.1 mol) was added and the mixture was stirred for 15 minutes. The mixture was then cooled to 0° C. in an ice bath and to it was added di-tert-butyl-dicarbonate (1102 grams, 5.05 mol) in portions. The mixture was allowed to stir overnight. Ethyl acetate (1.5 liters) was added to the reaction mixture followed by 6N HCl until the pH was <3 (caution: gas evolution.) The layers were allowed to separate and the aqueous layer was removed. The organic layer was dried over magnesium sulfate, then was concentrated under reduced pressure to give an oil. Mass recovery was approximately 770 grams (90% yield).

Tri-Boc Lysine-β-aminoethyl Ester (ref. 22117-52)

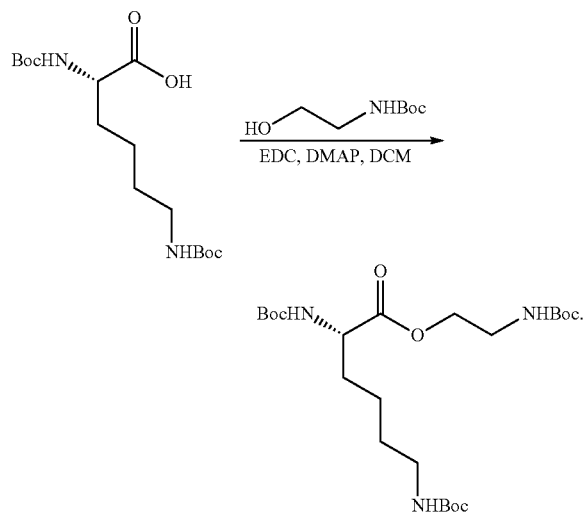

Di-Boc lysine (770 grams, 2.2 mol) was dissolved in dichloromethane (4 liters). Bocethanolamine (340 grams, 2.1 mol) was added to the solution, along with 4-dimethylaminopyridine (50 grams.) EDC-HCl (450 grams, 2.35 mol) was added and the mixture was allowed to stir overnight at room temperature. Water (2 liters) was added and the mixture was stirred for 30 minutes. The layers were separated, and the aqueous layer was extracted with dichloromethane. The combined organics were washed with saturated sodium bicarbonate, 1N HCl solution, and brine. Solvent was removed under reduced pressure to give an oil. Mass recovery was 770 grams (68% yield).

Lysine-β-aminoethyl Ester Trihydrochloride (ref. 22117-68)

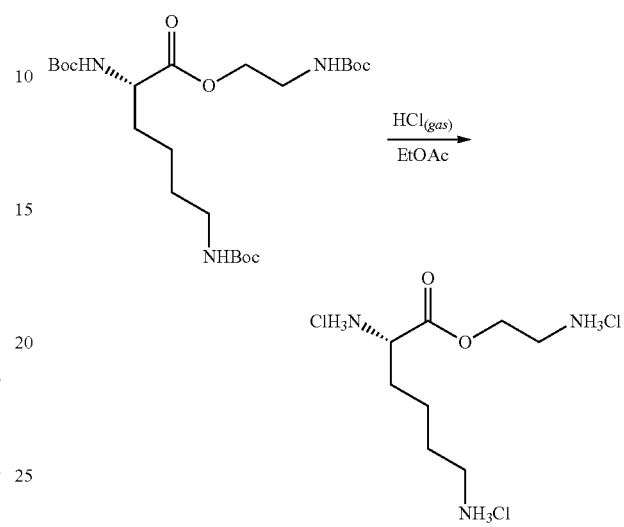

Tri-Boc Lysine-β-aminoethyl ester (770 grams, 1.57 mol) was dissolved in ethyl acetate (7 liters). HCl gas was bubbled through the solution for 2.5 hours then was stirred overnight at room temperature. The reaction mixture was decanted and the reactor was washed with fresh ethyl acetate. Methanol (2.5 liters) was added and the mixture was heated to 55° C. to dissolve "solids." 2-propanol (2.5 liters total) was added in portions, over 1 hour, while maintaining temperature at 55° C. The mixture was allowed to cool, and a white solid formed. Solids were isolated by vacuum filtration and dried in a vacuum oven. Mass recovery was 350 grams (75% yield).

Example 2

Preparation of Lysine Ester Triisocyanate (LTI) Using Diphosgene (ref. 70965-4)

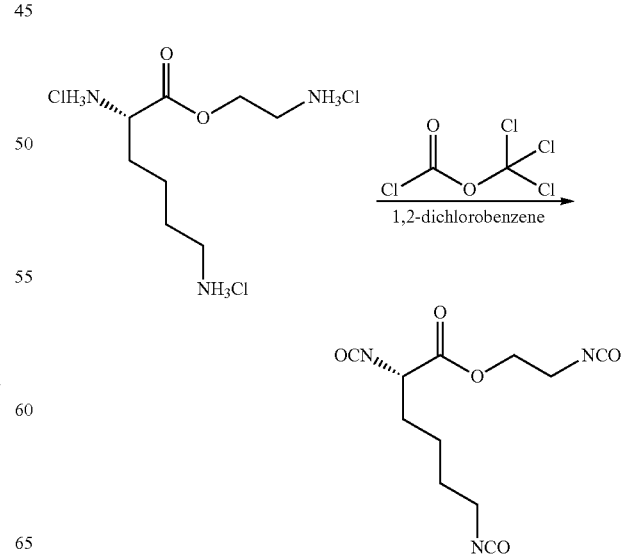

Lysine-β-aminoethyl ester trihydrochloride ("trihydrochloride salt", 10.0 grams, 33 mmol) was suspended in 1,2-dichlorobenzene (200 mL). The suspension was heated to 135° C. Diphosgene (50 ml, 420 mmol) was added to the hot suspension via syringe pump over approximately 4 hours. The resulting thin suspension was cooled and sparged with nitrogen to remove any residual phosgene. The mixture was then filtered and concentrated under reduced pressure to give a dark amber oil. The oil was dissolved in toluene (50 mL) and decolorized with activated carbon (1.5 grams). A light yellow oil was recovered after concentration under reduced pressure. Mass recovery was 7.7 grams (88% yield).

Example 3

Purification of Commercial LTI (ref. 53456-13)

Crude LTI (3020 grams) was weighed into a flask and combined with methyl tert-butyl ether (21.5 liters.) Activated carbon (600 grams, previously dried in a vacuum oven at 85° C.) was added and the mixture stirred for 30 minutes. The mixture was filtered through a glass fiber filter pad (Whatman 934-AH) and the filtrate was isolated and concentrated under reduced pressure to give an amber oil. Mass recovery was 2614 grams.

The oil was charged to a Pope still and distilled under the following initial conditions: temperature was 135 to 141° C.; pressure was 0.00 mm Hg (limit of meter); spinning band rate was 15/100; and feed rate was approximately 100 ml per hour.

Distillation was run under these conditions for 10 hours, then the temperature was increased to 160° C., and the spinning rate to 20-30/100 until all material was distilled.

Two fractions were collected after the distillation was complete. These fractions were as follows:
1. Non-boiling residue: 1035 grams as a brown viscous oil.
2. Distilled fraction: 1471 grams as a bright yellow oil.

The distilled fraction was carried forward and charged back into the Pope still. In this distillation, the following conditions were used: Temperature was 98 to 104° C.; Pressure was −0.08 mm Hg; Spinning rate was 15-20/100; Feed rate was approximately 75-100 ml per hour.

Again, two fractions were collected. These fractions were as follows:
1. Non-boiling residue: 1300 grams as a light yellow-green oil.
2. Distilled fraction: ~160 grams as a pale-yellow oil.

At this point, the non-boiling residue was determined to be of acceptable quality and was used as is for generation of pre-polymer. A third distillation using the higher temperature conditions shown above would have reduced both 1,2-dichlorobenzene and "methyl ester" impurities to negligible levels, but would have also significantly reduced recovery (by as much as 30%).

Example 4

Purification of Produced LTI

The LT1 produced by the procedure described in example 2 above was isolated as a clear amber oil. Crude LTI was purified by vacuum distillation using a short-path distillation head, with purified LTI obtained as a pale-yellow viscous oil. The boiling point of LTI at atmospheric pressure was estimated to be approximately 400° C. based on the observed boiling point of 165-170° C. at 0.41 mm Hg. Distillation required very high temperatures, and significant decomposition was evident in the boiling flask.

As comparision, commercial sources for LTI were identified. The commercially available material appeared to be significantly less pure than that which was produced in Example 2. The purchased LTI was a relatively thin liquid resembling used motor oil, very different from the clear amber oil prepared in the lab. An initial attempt at purification of commercial LTI using a Pope still was unsuccessful. It appeared that the crude LTI contained higher molecular weight impurities which formed a crust in the Pope still and destroyed the glass still body. This problem was solved by employing a pre-purification step using methyl tert-butyl ether (MTBE) and activated carbon. The use of MTBE was important since it appeared that the high molecular weight impurities had little solubility in MTBE and coagulated on the sides of the container during dissolution. By adding activated carbon, the resulting gelatinous impurities were adsorbed and easily removed by vacuum filtration. After concentration of the MTBE solution LTI similar in appearance to that prepared in Example 2 was obtained. However, testing showed that the material was not of acceptable quality for use without further purification.

Once the higher molecular weight impurities had been reduced, the material was easily distilled in the Pope still. The preferred sequence that was developed for the distillation was as follows. The crude oil recovered from the carbon treatment was distilled at high vacuum (<0.01 mm Hg, 155-165° C.), collecting the volatile fraction and discarding the non-volatile residue. This appeared to remove any remaining high boiling components and gave a much cleaner intermediate product. The first distillation was followed by another pass through the Pope still at 95-105° C. (<0.01 mm Hg). This treatment removed the "methyl ester" impurity, which has a slightly lower boiling point than LTI, and removed any residual o-dichlorobenzene. The desired compound was collected as the non-volatile residue. Finally, the distillation was repeated using the original conditions and the LTI was isolated as the volatile component. This sequence is shown in FIG. 1.

Once conditions for the distillation sequence were identified, our attention shifted to the large-scale purification of commercial LTI. Ten kilograms of crude LTI, purchased from Infine, was purified as described above. Total recovery of purified LTI was approximately 4500 grams, and this material served as the regulatory starting material (RSM) for the cGMP preparation of the LTI-PEG200 pre-polymer.

Example 5

Preparation of LTI-PEG-200 Pre-Polymer

Several small-scale experiments were conducted which examined the effect of order of addition of reagents on the level of residual LTI that remained in the pre-polymer. In some experiments, LTI was added slowly to a heated quantity of PEG-200. In other experiments, the order of addition was reversed (i.e., PEG-200 added to a heated sample of LTI). There was no significant difference in the levels of unreacted LTI that remained in the final pre-polymer samples. The latter method was chosen for the bulk sample preparation since, intuitively, this method may minimize LTI reaction with PEG-200 and not consume all free hydroxyls (which would leave LTI added late in the reaction without reactive sites.) Without wishing to be bound to particular theory, it is proposed that the latter method (i.e., PEG added into LTI) may be advantageous on larger scale of manufacturing, where addition times will be longer and temperature control more difficult due to viscosity.

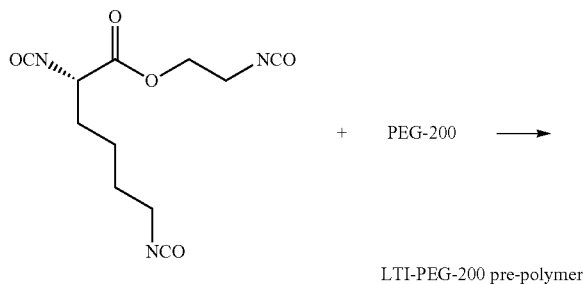

+ PEG-200 → LTI-PEG-200 pre-polymer

Purified LTI (165 grams) was placed into a 500 mL Pyrex jar fitted with a mechanical stirrer and nitrogen inlet. The vessel was heated to 80° C. PEG-200 (62 grams) was taken up into a syringe and placed into a syringe pump. The PEG-200 was added to the stirred LTI via syringe pump over 1 hour. Heating was continued for an additional 2 hours. The stirrer was removed and the jar flushed with nitrogen and sealed. The material was recovered as a golden, low-viscosity oil. Viscosity increased considerably on cooling.

A cGMP preparation of LTI-PEG-200 was also conducted. In this run, LTI (4.52 kg) was reacted with PEG-200 (1.70 kg) as described above. The material was transferred while at 80° C. using an Argon pad. A total of 6.1 kg of the LTI-PEG-200 pre-polymer was recovered.

All references, such as patents, patent applications, and publications, referred to above are incorporated by reference in their entirety.

Still other embodiments are within the scope of the following claims.

What is claimed is:

1. A method of synthesizing an isocyanate comprising a step of reacting a phosgene substitute or precursor with a trihydrochloride salt of an amine.

2. The method of claim 1, wherein the step of reacting is processed in a two-reactor system.

3. The method of claim 2, wherein the step of reacting comprises adding the phosgene substitute or precursor in a controlled manner into a suspension of a catalyst to produce phosgene gas in a first reactor.

4. The method of claim 3, wherein the phosgene substitute or precursor is or comprises diphosgene.

5. The method of claim 3, wherein the phosgene substitute or precursor is added by a syringe pump or a dropping funnel.

6. The method of claim 3, wherein the catalyst comprises activated carbon.

7. The method of claim 3, wherein the suspension in the first reactor is heated and stirred.

8. The method of claim 3, wherein the suspension in the first reactor is heated to approximately 135° C.

9. The method of claim 3, wherein the suspension in the first reactor is heated to approximately 125-310° C.

10. The method of claim 3, wherein the suspension in the first reactor comprises a solvent.

11. The method of claim 10, wherein the solvent is or comprises o-dichlorobenzene.

12. The method of claim 2, wherein the step of reacting comprises transferring the phosgene gas produced in the first reactor to a second reactor into a suspension of the trihydrochloride salt of the amine.

13. The method of claim 12, wherein the suspension in the second reactor is heated and stirred.

14. The method of claim 12, wherein the suspension in the second reactor is heated to approximately 135° C.

15. The method of claim 12, wherein the suspension in the second reactor is heated to approximately 125-310° C.

16. The method of claim 12, wherein the suspension in the second reactor comprises a solvent.

17. The method of claim 16, wherein the solvent is or comprises o-dichlorobenzene.

18. The method of claim 1, wherein the step of reacting comprises adding the phosgene substitute or precursor in a controlled manner into a suspension of the trihydrochloride salt of the amine.

19. The method of claim 1, further the comprising the step of fractionally removing impurity from the synthesized isocyanate by distillation.

20. The method of claim 1, wherein the trihydrochloride salt of the amine comprises lysine-β-aminoethyl ester trihydrochloride.

* * * * *